United States Patent
Esteve

(10) Patent No.: US 11,951,247 B2
(45) Date of Patent: Apr. 9, 2024

(54) DRY POWDER INHALER

(71) Applicant: Emphasys Importadora Exportadora e Distribuidora Ltda., Porto Feliz Sp (BR)

(72) Inventor: Victor Esteve, Itu (BR)

(73) Assignee: EMPHASYS LMPORTADORA EXPORTADORA E DISTRIBUIDORA LTDA., Porto Feliz SP (BR)

(*) Notice: Subject to any disclaimer, the term of this patent is extended or adjusted under 35 U.S.C. 154(b) by 969 days.

(21) Appl. No.: 16/772,083

(22) PCT Filed: Dec. 13, 2017

(86) PCT No.: PCT/IB2017/001562
§ 371 (c)(1),
(2) Date: Jun. 11, 2020

(87) PCT Pub. No.: WO2019/116061
PCT Pub. Date: Jun. 20, 2019

(65) Prior Publication Data
US 2021/0069432 A1   Mar. 11, 2021

(51) Int. Cl.
*A61M 15/00* (2006.01)

(52) U.S. Cl.
CPC ...... *A61M 15/003* (2014.02); *A61M 15/0026* (2014.02); *A61M 2202/064* (2013.01)

(58) Field of Classification Search
CPC .. A61M 15/0021; A61M 15/0025–003; A61M 15/0033–0035; A61M 15/0038; A61M 15/0041
See application file for complete search history.

(56) References Cited

U.S. PATENT DOCUMENTS

| 5,947,118 A | 9/1999 | Hochrainer et al. |
| 6,070,749 A * | 6/2000 | Joulia ............... A45D 40/221 |
| | | 220/817 |

(Continued)

FOREIGN PATENT DOCUMENTS

| CN | 103237570 A | 8/2013 |
| CN | 103415315 A | 11/2013 |

(Continued)

OTHER PUBLICATIONS

International Search Report for appln. No. PCT/IB2017/001562 dated Aug. 6, 2018.

(Continued)

*Primary Examiner* — Rachel T Sippel
(74) *Attorney, Agent, or Firm* — Carter, DeLuca & Farrell LLP

(57) ABSTRACT

It is provided a dry powder inhaler (2) for a capsule containing dry powder, the dry powder inhaler (2) comprises: a mouth piece (14) with a mouth portion, wherein an opening of the mouth portion leads into a duct; a one-piece base body (10) comprising a capsule chamber portion and being attached to a covering body (6); and an actuator button (8) movable relative to the one-piece base body (10) from a normal position to a perforation position along an actuation direction, wherein the actuation direction is perpendicular to the longitudinal axis, and wherein perforation needles attached to the actuator button (8) extend into the capsule chamber when the actuator button (8) is in the perforation position.

14 Claims, 9 Drawing Sheets

(56) References Cited

U.S. PATENT DOCUMENTS

| | | | |
|---|---|---|---|
| 11,400,242 B2 * | 8/2022 | Ziegler | A61M 15/0051 |
| 2007/0240713 A1 | 10/2007 | Boeck | |
| 2009/0165791 A1 * | 7/2009 | Wendland | A61M 15/0026 |
| | | | 128/203.21 |
| 2011/0232637 A1 * | 9/2011 | Kaemper | A61M 15/0028 |
| | | | 128/203.12 |
| 2013/0255679 A1 * | 10/2013 | Andrade | A61M 15/08 |
| | | | 128/203.15 |
| 2018/0043111 A1 * | 2/2018 | Ahern | A61M 15/003 |
| 2019/0076607 A1 * | 3/2019 | Zeng | A61M 11/003 |

FOREIGN PATENT DOCUMENTS

| | | |
|---|---|---|
| CN | 104245025 A | 12/2014 |
| GB | 2151491 A | 7/1985 |
| WO | 02084501 A1 | 10/2002 |
| WO | 03084502 A1 | 10/2003 |
| WO | 2015054124 A2 | 4/2015 |

OTHER PUBLICATIONS

Notification of Transmittal of International Preliminary Report on Patentability dated Apr. 21, 2020.
Chinese Office Action for application No. 201780097702.8 dated Mar. 15, 2023 with English translation.
Taiwan Search Report for application No. 107144797 completion date Nov. 22, 2012.with English Translation, 2 pages.

* cited by examiner

DRY POWDER INHALER

FIELD OF THE INVENTION

The present invention relates to a dry powder inhaler.

BACKGROUND

U.S. Pat. No. 5,947,118 discloses a capsule holder for the insertion and fixing of pharmaceutical capsules consists of a plate with a recess in which there are at least three ribs arranged parallel to the central axis and at unequal spacings from one another, between which the capsules can be clamped both by their upper part and by their lower part in such a way that they do not fall out during normal handling but can readily be removed.

GB2151491 discloses an inhalation apparatus for the inhalation of pulverulent material, especially micronized pharmaceutical compositions from capsules. A chamber for receiving the capsules is provided, which has an internal width about 1.1 to 2.5 times the capsule diameter and an internal length of at least about 1.02 and less than 2.0 times the length of the capsule and which comprises at one narrow end an air inlet and at the other end an air outlet, so that during inhalation through the inhalation apparatus the capsule is set in vibration providing enhanced expulsion and fragmentation of the pulverulent material.

WO2015054124 discloses a dry powder inhaler comprising: a dry powder medicament comprising fluticasone propionate, salmeterol xinafoate and a lactose carrier; wherein, the delivered dose of salmeterol per actuation is less than 50 µg; and wherein the dose provides a baseline-adjusted FEV1 in a patient of more than 150 mL within 30 minutes of receiving the dose.

WO03084502 discloses a method for the administration of powdered preparations containing tiotropium via inhalation.

US2007240713 discloses an inhaler for administering a medicament in the form of inhalable substances, formulations or mixtures of substances comprises a housing having an inner cavity for holding the medicament, which is coupled to a mouthpiece. The housing is rigidly connected to the mouthpiece.

SUMMARY

In view of this, it is an object of the present invention to provide an improved dry powder inhaler.

The problem of the prior art is solved by an inhaler according to claim 1.

According to an aspect it is provided a dry powder inhaler for a capsule containing dry powder. The dry powder inhaler comprises: a mouth piece with a mouth portion, wherein an opening of the mouth portion leads into a duct; a covering body; a one-piece base body comprising a capsule chamber portion and being attached to the covering body, wherein a base body opening, which is arranged towards the mouth piece, leads into a capsule chamber of the capsule chamber portion, wherein the duct and the capsule chamber extend along a common longitudinal axis when the mouth piece abuts the base body, and wherein a hinge directly connects the mouth piece and the one-piece base body; and an actuator button movable relative to the one-piece base body from a normal position to a perforation position along an actuation direction, wherein the actuation direction is perpendicular to the longitudinal axis, and wherein perforation needles attached to the actuator button extend into the capsule chamber when the actuator button is in the perforation position.

The one-piece base body provides a simplification in construction, therefore reducing manufacturing costs. Moreover, the dry powder inhaler is constructed to be more robust against damage and degradation by use.

According to an advantageous embodiment the dry powder inhaler comprises: an intermediate piece, which is attached to a distal end of the duct of the mouth piece; and a mesh piece, which is attached to the intermediate piece. The intermediate piece decouples the construction of the mouth piece from the construction of the mesh piece. Therefore, mold construction becomes more simple as metal over-injected parts or welded parts are avoided. Moreover, an inner diameter of the duct may remain small, independently of the construction of the mesh piece. The construction of the mesh piece comprises inter alia different opening structures in the sense of a mesh format. For example, chessboard-like, cobweb-like and cross-like opening structures have a different impact on the delivery profile of the powder formulation inside the lungs. The interchangeable mesh piece allows that the other parts of the inhaler remain unchanged. Consequently, a cheaper inhaler is provided but flexibility of delivery profile of the powder formulation is established.

According to an advantageous embodiment the intermediate piece is held only by means of a first ring snap connection, wherein the mesh piece is held only by means of a second ring snap connection. These ring snap connections provide a simplification of the manufacturing process and guarantee that the mesh remains connected to the duct.

According to an advantageous embodiment the one-piece base body comprises an annular-shaped groove arranged around the base body opening, and wherein the intermediate piece comprises an annular-shaped distal end for engaging with the annular-shaped groove. This provides a seal formed by the base body and the intermediate piece.

According to an advantageous embodiment an inner diameter of the intermediate piece and/or the mesh piece is greater than an inner diameter of the duct in order to provide air turbulences after passing the mesh piece.

According to an advantageous embodiment an inner diameter of the duct of the mouth piece is smaller than an inner diameter of the capsule chamber. This smaller inner diameter of the duct maximizes the efficiency by controlling the pressure and turbulence generated inside the capsule chamber. Particularly, the powder-air-mixture leaves the mouth-piece as a narrow, centralized stream. This narrow stream avoids a powder deposition in the throat area and therefore enhances the delivery of the powder formulation to the lower airways of the lung.

According to an advantageous embodiment the one-piece base body is attached to the covering body by means of a latching connection. An easy to manufacture and reliable connection between the base body and the covering body is provided.

According to an advantageous embodiment the one-piece base body comprises a ratchet of the latching connection, and an outer surface opposed to the ratchet; and wherein the covering body comprises a first inner protrusion for the third latching connection, the first inner protrusion comprising a hole receiving the ratchet of the one-piece base body, and a second inner protrusion abutting said outer surface of the one-piece base body. Advantageously, the ratchet provides a distal connection point of the base body inside the covering body.

According to an advantageous embodiment the covering body further comprises an opening with an inward cut-out for receiving a plate portion of the one-piece base body, and wherein the one-piece base body further comprises the plate portion with an outward edge contacting at least partly the inward cut-out. Therefore, a form-fit is provided in a plane perpendicular to the common longitudinal axis.

According to an advantageous embodiment the actuator button comprises guiding members, which protrude from a button body, and embrace at least partly the capsule chamber portion. Advantageously, the guiding members are guided by means of the capsule chamber portion, therefore providing a simple guiding construction for the actuator button.

According to an advantageous embodiment a guiding channel is formed for each guiding member by an inner support protrusion of the covering body and the capsule chamber portion. A simplified guiding construction is provided for the actuator button.

According to a further aspect a method of manufacturing the dry powder inhaler is provided. The method comprises: attaching the intermediate piece to the distal end of the duct of the mouth piece; attaching the mesh piece to the intermediate piece; attaching the actuator button to the one-piece base body; attaching the one-piece base body to the covering body; and attaching the mouth piece to the one-piece base body to provide the hinge.

According to yet another aspect a dry powder inhaler for a capsule containing dry powder is provided. The dry powder inhaler comprises: a mouth piece with a hinge section; a covering body; a one-piece base body comprising a capsule chamber portion and being attached to the covering body, wherein a hinge directly connects the mouth piece and the one-piece base body, wherein the hinge section of the mouth piece is connected to a hinge section of the one-piece base body via a ball joint snap-on connection for pivoting around a hinge axis. Advantageously the snap-on connection provides that further elements like additional pins or the like to provide the hinge are omitted.

According to an advantageous embodiment the hinge axis of the hinge is arranged in an inclined angle within the range of 40° to 50° with respect to the actuation direction.

According to an advantageous embodiment the hinge axis is arranged in a plane perpendicular to a central longitudinal axis of the inhaler.

DESCRIPTION OF THE EMBODIMENTS

Figure 1:
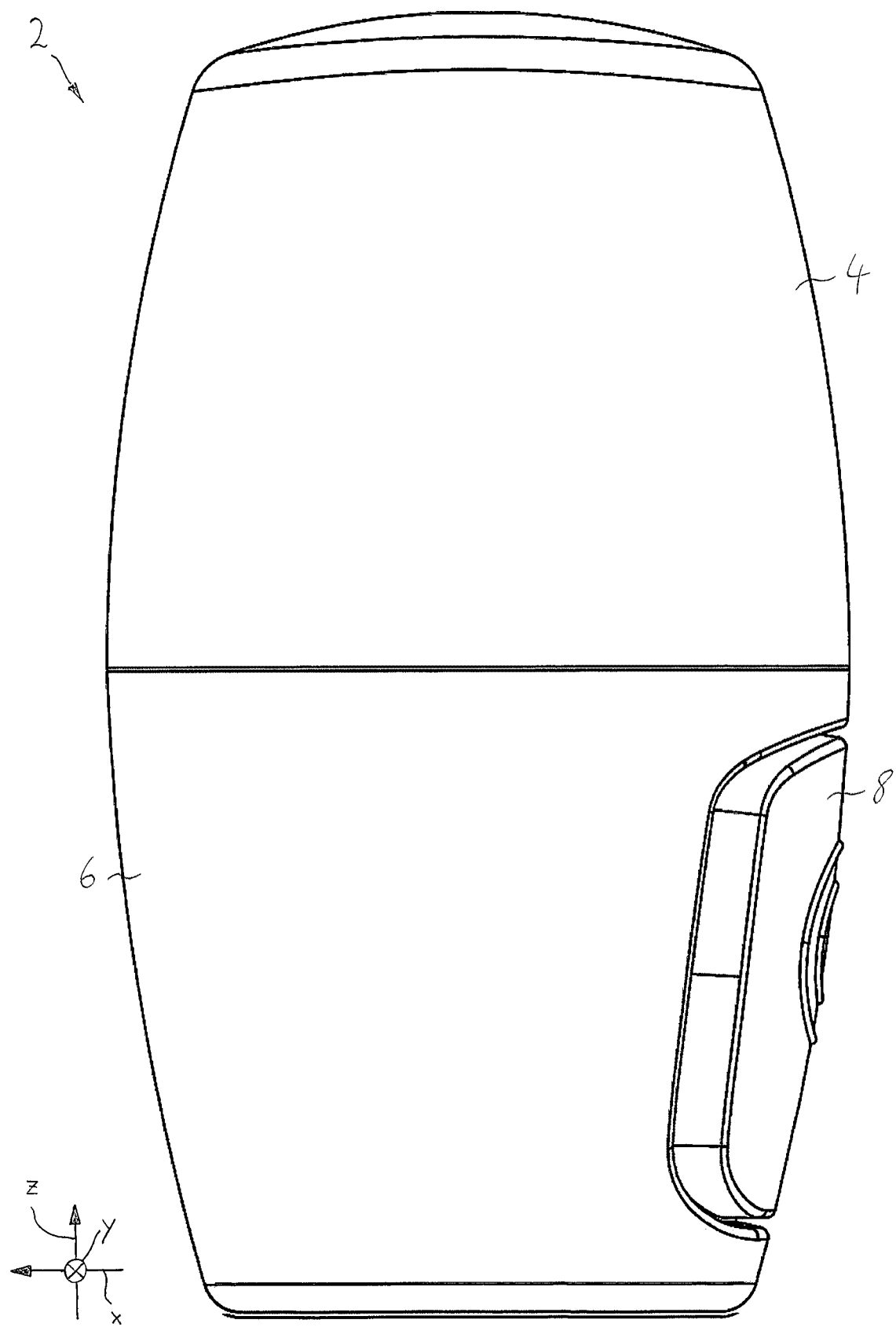
FIG. 1 is a schematic side view of a closed dry powder inhaler.

FIG. 1 is a schematic side view of a closed dry powder inhaler 2. The dry powder inhaler 2 comprises an overcap 4, a covering body 6 and an actuator button 8.

Figure 2:
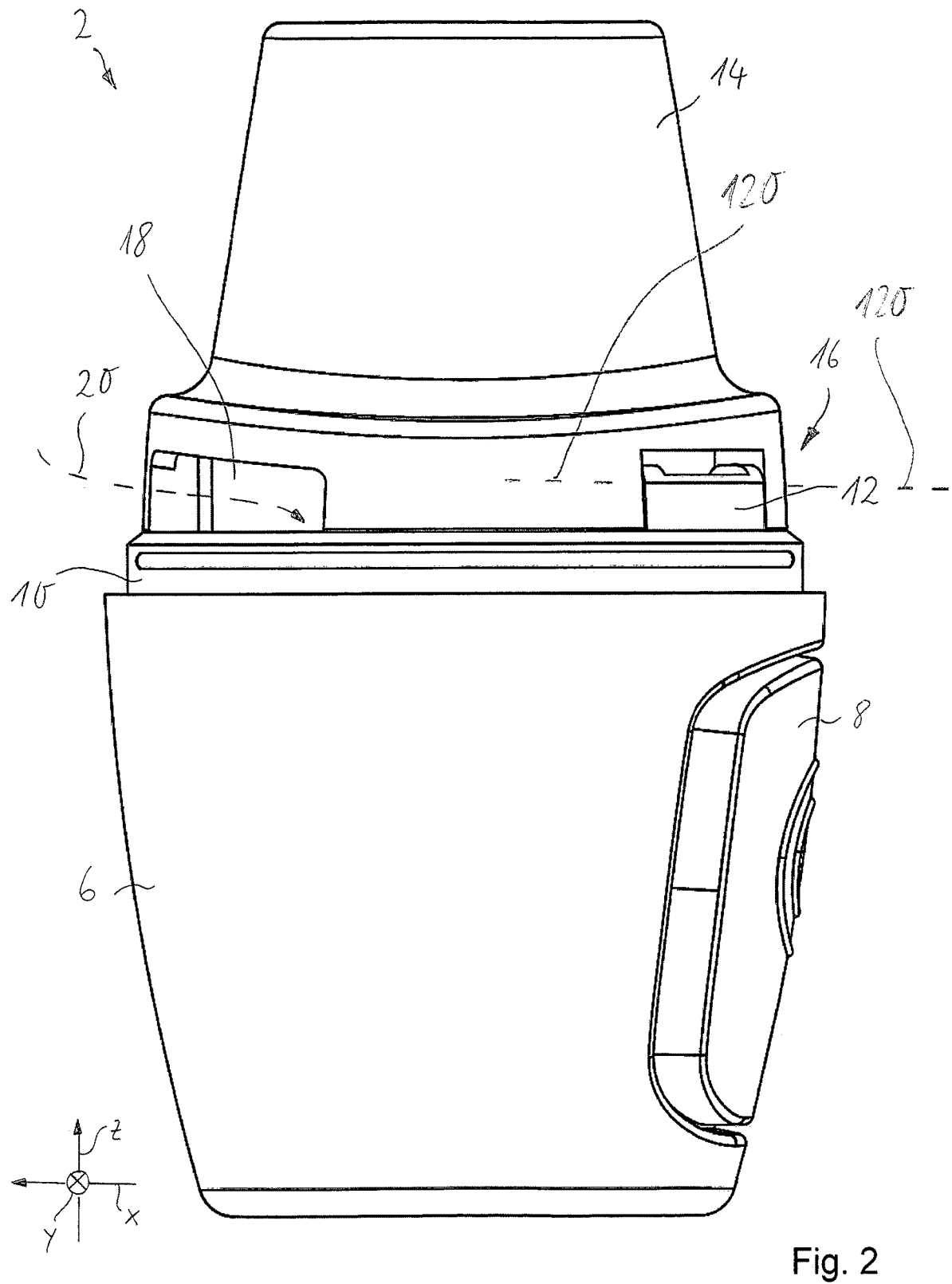
FIG. 2 is a schematic side view of the dry powder inhaler without an overcap.

FIG. 2 is a schematic side view of the dry powder inhaler 2 without the overcap 4 of FIG. 1. A one-piece base body 10 is attached to the covering body 6 and extends partially into the covering body 6. A hinge section 12 protrudes from the base body 10 in z-direction. A further hinge section of a mouth piece 14 locks with the hinge section 12 and provides a hinge 16 between the mouth piece 14 and the base body 10. The hinge 16 provides that the mouth piece 14 is rotatable around an axis 120 and relative to the base body 10.

Both the base body 10 and the mouth piece 14 enclose an opening 18 which leads into an interior space between the covering body 6 and the base body 10. According to an arrow 20 air can flow from an outside of the inhaler 2 into an inner volume between the base body 10 and the covering body 6.

Figure 3:
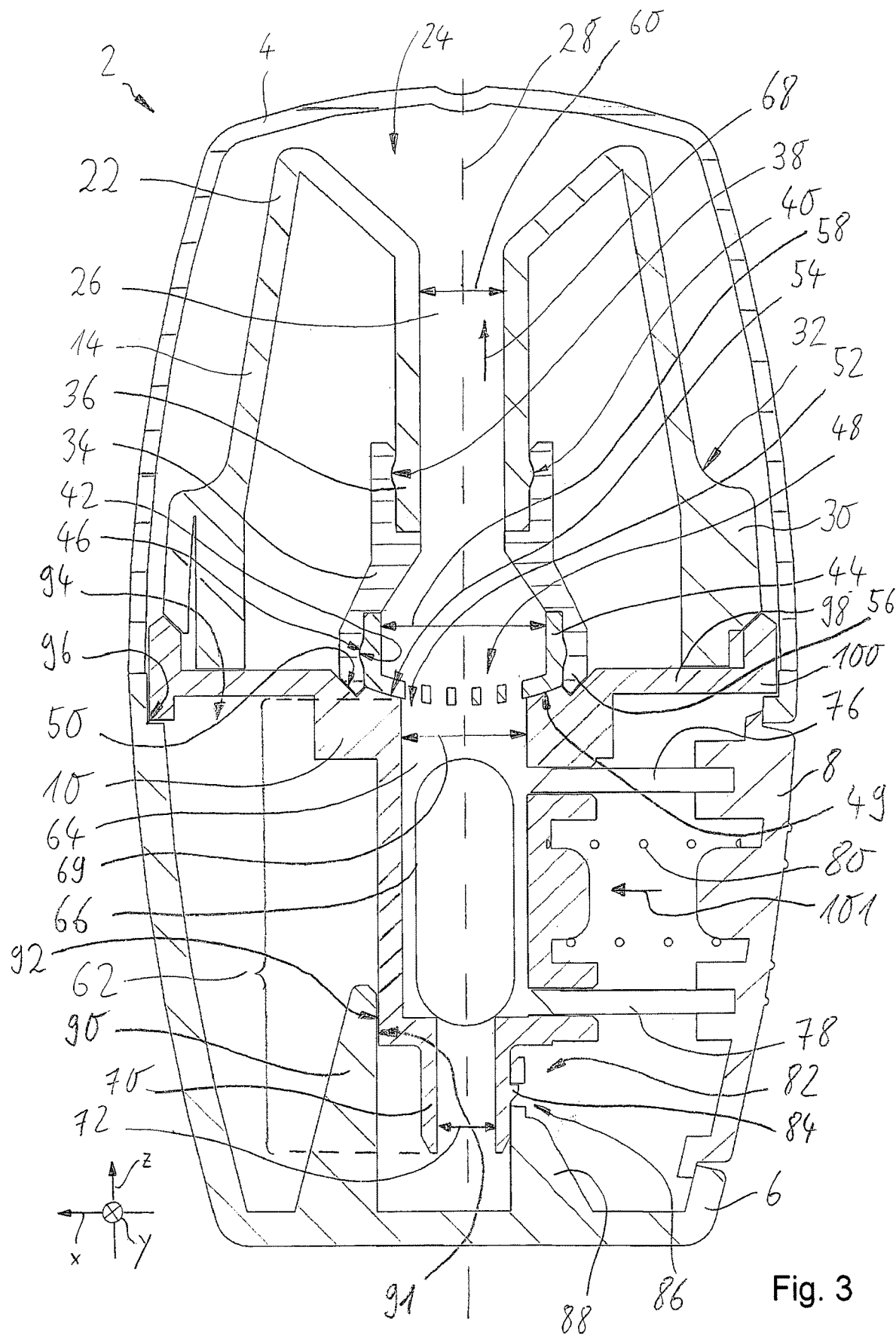
FIG. 3 is a schematic sectional view of the inhaler in an xz plane.

FIG. 3 is a schematic sectional view of the inhaler 2 according to a central plane xy of the inhaler 2. The mouth piece 14 comprises a mouth portion 22 with an opening 24, the opening 24 leading into a cylinder-shaped duct 26. The duct 26 extends along a central longitudinal axis 28 of the inhaler 2. A further opening of the duct 26 is arranged towards the base body 10. The mouth piece 14 comprises a base section 30 for engaging with the base body 10. A concave recess 32 is arranged between the base section 30 and the mouth portion 22.

An intermediate piece 34 is attached to a distal end 36 of the duct 26. An annular-shaped outer protrusion 40 at the outer surface of the distal end 36 engages an annular-shaped inner recess 38 of the intermediate piece 34 which is a form-fit. The recess 38 is arranged in a hole of the intermediate piece 34, the hole extending along the longitudinal axis 28 with an opening arranged towards the mouth portion 22. Therefore, a ring snap connection between the intermediate piece 34 and the mouth piece 14 is provided.

An annular-shaped outer protrusion 42 of a mesh piece 44 engages an annular-shaped inner recess 46 of the intermediate piece 34 which is a form-fit. The recess 46 is arranged in a hole of the intermediate piece 34, the hole extending along the longitudinal axis 28 with an opening arranged towards the base body 10. The mesh piece 44 comprises a mesh 48 which inhibits larger particles from entering the duct. Therefore, a ring snap connection between the intermediate piece 34 and the mesh piece 44 is provided. The mesh piece 44, the intermediate piece 34 and the mouth piece 14 are preferably made of plastic material.

In the shown closed position of the mouth piece 14 an outer annular-shaped surface 49 of mesh piece 44 abuts an opposing annular-shaped surface 54 of the base body 10. The surface 49 faces towards the base body 10. The annular-shaped surface 54 is surrounded by an annular-shaped groove 50 of the base body 10. A distal annular-shaped projection 56 of the intermediate piece 34 engages the groove 50.

The intermediate piece 34 has an inner diameter increase in the opposite direction to the z-direction, namely the inhalation direction 68, leading to the inner diameter 58. The inner diameter 58 is provided by the mesh piece 44 and allows for increased air turbulences when a mixture of air and dry powder passes the mesh 48. The inner diameter 58 also allows that the mesh 48 has a diameter which is at least as large as the inner diameter 60 of the duct 36.

A capsule chamber portion 62 of the base body 10 comprises a capsule chamber 64 and an air inlet section 70, which extends along the longitudinal axis 28. The air inlet section 70 is in fluid connection with the ambient area of the inhaler 2. The capsule chamber 64 extends along the longitudinal axis 28. The capsule chamber 64 has an inner diameter 69 which is larger than the inner diameter 60 of the duct 36 but smaller than the inner diameter 58 of the mesh piece 44. The air inlet section 70 comprises a through-hole connecting the capsule chamber 64 with the interior space between the covering body 6 and the base body 10. The through-hole of the air inlet section 70 has an inner diameter 72 which is smaller than the inner diameter 69, therefore providing a seat for a capsule 66 and providing that air can enter the capsule chamber 64 in the inhalation direction 68. The capsule chamber 64 and the duct are configured around the central common axis 28.

The air inlet section 70 comprises an outer ratchet 84 protruding perpendicularly to the axis 28 from an outer surface of the air inlet section 70. The ratchet 84 snaps into a hole 86, which extends perpendicularly to the axis 28 and which is part of a first inner projection 88 of the covering body 6. The ratchet 84 and the opening therefore provide a snap-on connection 82 to establish a form-fit in the z-direction. The first inner projection 88 protrudes parallel to the axis 28 into the interior space of the covering body 6. The outer surface of the air inlet section 70 abuts at least partly a surface of the first inner projection.

A second inner projection 90 protrudes parallel to the axis 28 into the interior space of the covering body. The second inner projection 90 provides a surface 91 abutting an outer surface 92 of the capsule chamber portion 62. The surface 91 thus provides a counterpart for the abutting surfaces at the snap-on connection 82. The abutting surfaces between the capsule chamber portion 62 and the projections 88 and 90 provide a form-fit along the x-axis.

For the permanent attachment of the base body 10 to the covering body 6, the covering body 6 provides an inner annular-shaped cut-out 96 at a first opening 94 of the covering body. The base body 10 comprises a plate portion 98 for closing the opening 94. An edge 100 of the plate portion 98 engages in the cut-out 96 providing a form-fit in the direction against the z-direction and in an xy-plane. The snap-on connection 82 and the elements like the ratchet 8 involved are matching with the cut-out 96 and the edge 100 in order to provide a safe attachment of the covering body 6 to the base body 10.

The actuator button 8 is guided in the interior space between the covering body 6 and the base body 10. Two perforation needles 76, 78 extend perpendicularly to the axis 28 and are arranged in the middle plane xz of the inhaler 2. The actuator button 8 is movable relative to the one-piece base body 10 from a normal position, as shown, to a perforation position along an actuation direction 101. The actuation direction 101 is perpendicular to the longitudinal axis 28. The perforation needles 76, 78 attached to the actuator button 8 extend into the capsule chamber when the actuator button is in the perforation position. A helical spring 80 is arranged between the base body 10 and the actuator button 8 in order to bring the actuator button 8 from the perforation into the normal position when the actuator button 8 is not being actuated.

In case of a rotation of the mouth piece 14 about the hinge, the mouth piece 14 releases the opening 52 of the capsule chamber 64. Through the opening 52, the capsule 66 is introduced into the capsule chamber 64. Then the mouth piece 14 is rotated about the hinge to close the opening 52. By using the actuator button 8 the capsule 66 is pierced at its opposing ends in order to release the dry powder from the capsule 66 to the capsule chamber 64. Then the person inhales the powder-air mixture by enclosing the mouth portion 22 with his lips and sucking the powder-air mixture into his lungs.

Figure 4:
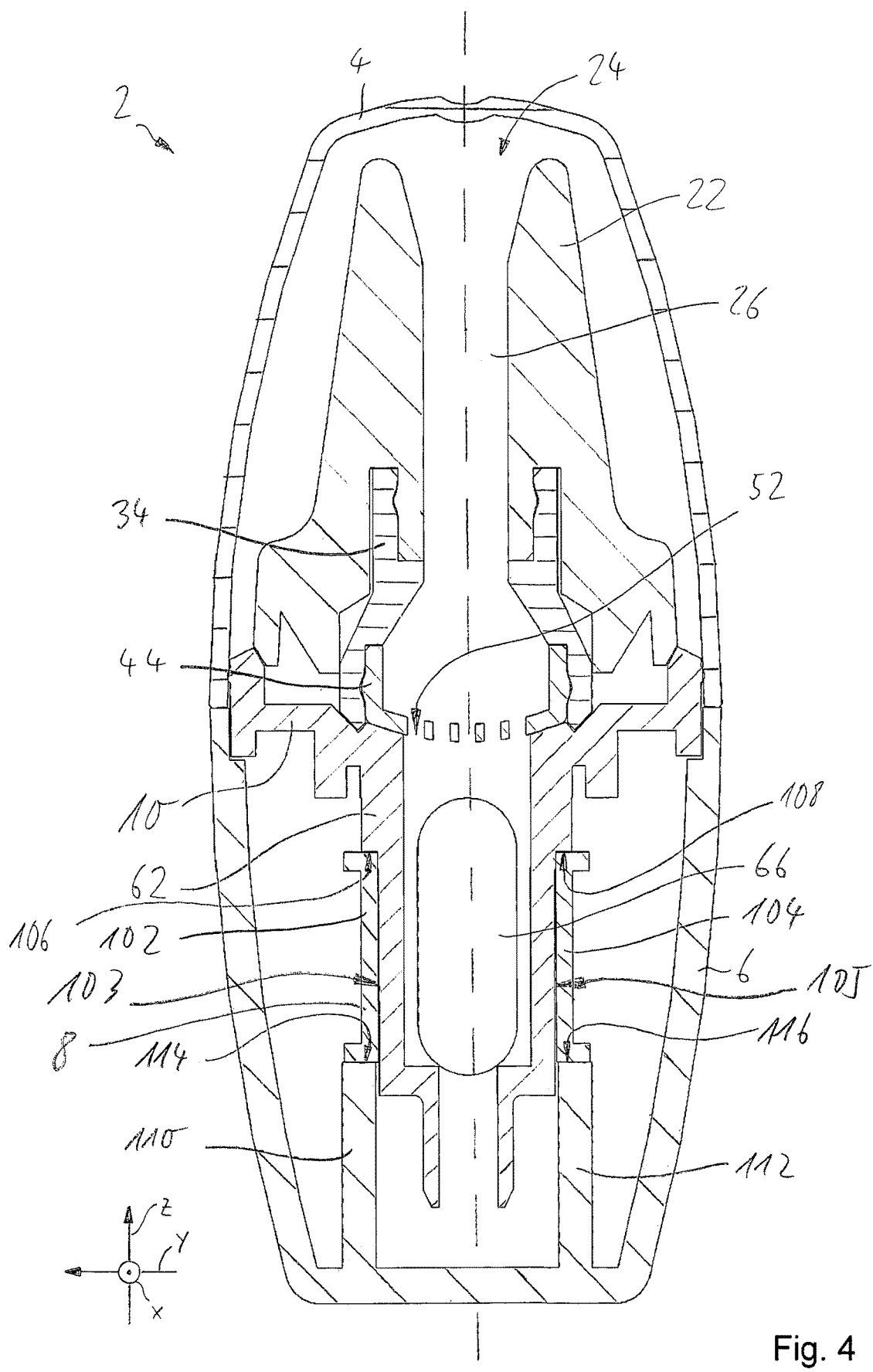
FIG. 4 is schematic sectional view of the inhaler in an yz plane.

FIG. 4 is a schematic sectional view of the inhaler 2 in an yz-plane. The actuator button 8 comprises guiding members 102 and 104, which protrude from a button body of the actuator button in the x-direction and the actuator button 8 being movable along the x-axis. The guiding members 102 and 104 embrace at least partly the capsule chamber portion 62, wherein the capsule chamber portion 62 provides outer guiding surfaces 103 and 105. The surfaces 103 and 105 face away from each other. Therefore the guiding members 102, 104 and the capsule chamber portion 62 provide a form-fit along the y-axis. Guiding channels are formed for each guiding member 102, 104 by inner support protrusions 110 and 112 of the covering body 6 and an L-shaped cut-out of the capsule chamber portion 62. The L-shaped cut-out comprises a respective surface 106, 108 facing away from the opening 52 of the capsule chamber 64. The protrusions 110, 112 comprise respective surfaces 114, 116 facing to the opening 52. The capsule chamber portion 62 and the protrusion 110 enclose the guiding member 102 providing a form-fit along to the z-axis. The capsule chamber portion 62 and the protrusion 112 enclose the guiding member 104 providing a form-fit along to the z-axis.

Figure 5:
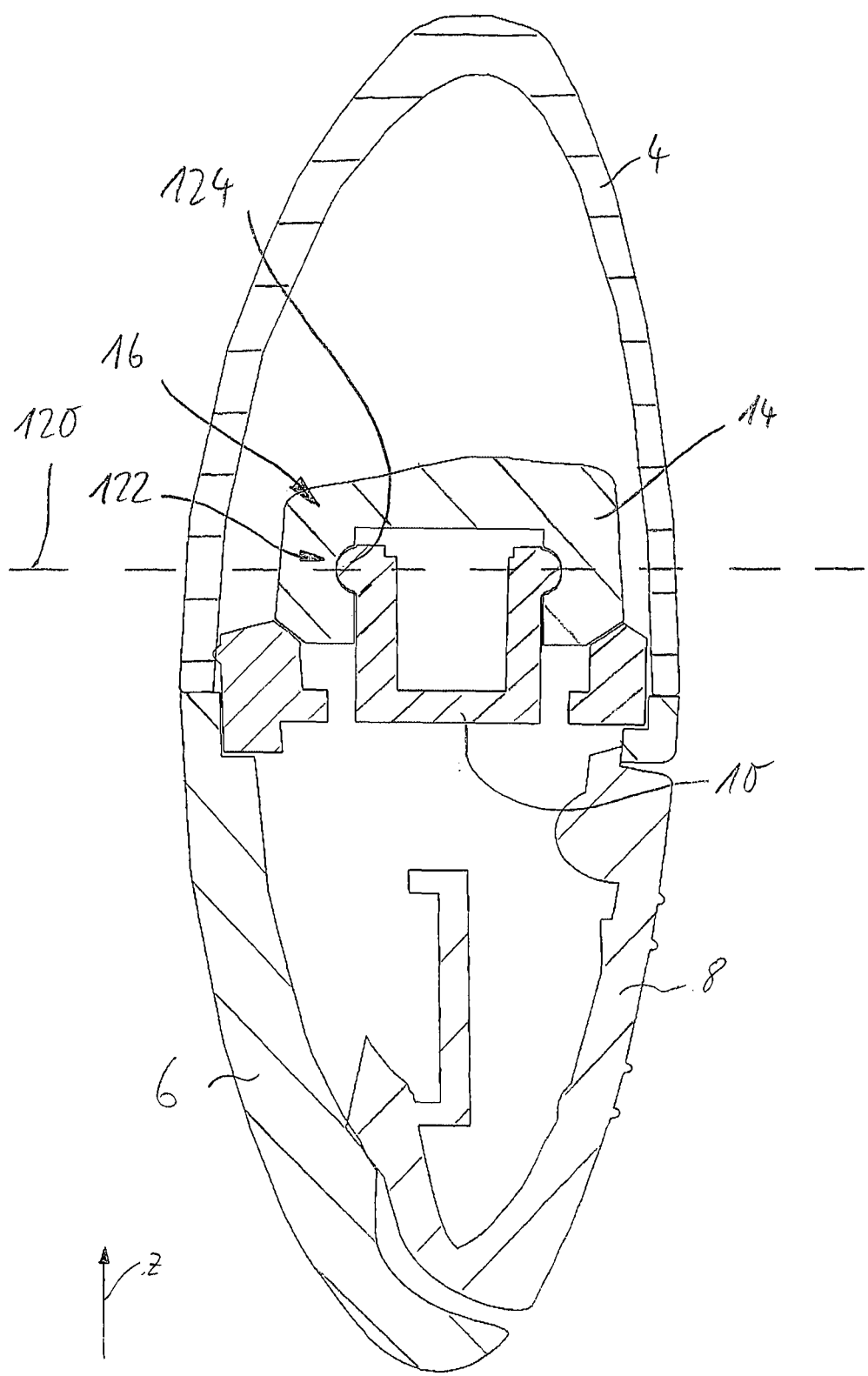
FIG. 5 is a schematic sectional view of the inhaler showing a hinge.

FIG. 5 is a schematic sectional view of the inhaler 2 showing the hinge 16. The hinge axis 120 of the hinge 16 is arranged in an inclined angle within the range of 40° to 50° with respect to the actuation direction x. The hinge axis 120 is arranged in the xy plane and therefore in a plane perpendicular to the longitudinal axis 28 of the preceding FIGS. 3 and 4. The hinge section 122 of the mouth piece 14 comprises two hemispherical cut-outs facing each other on the axis 120. A hinge section 124 of the base body 10 comprises two hemispherical protrusions facing away from each other in order to engage the corresponding hemispherical cut-outs. Therefore, a direct ball joint snap-on connection between the mouth piece 14 an the base body 10 is provided for pivoting the mouth piece 14 around the hinge axis 120.

Figure 6:
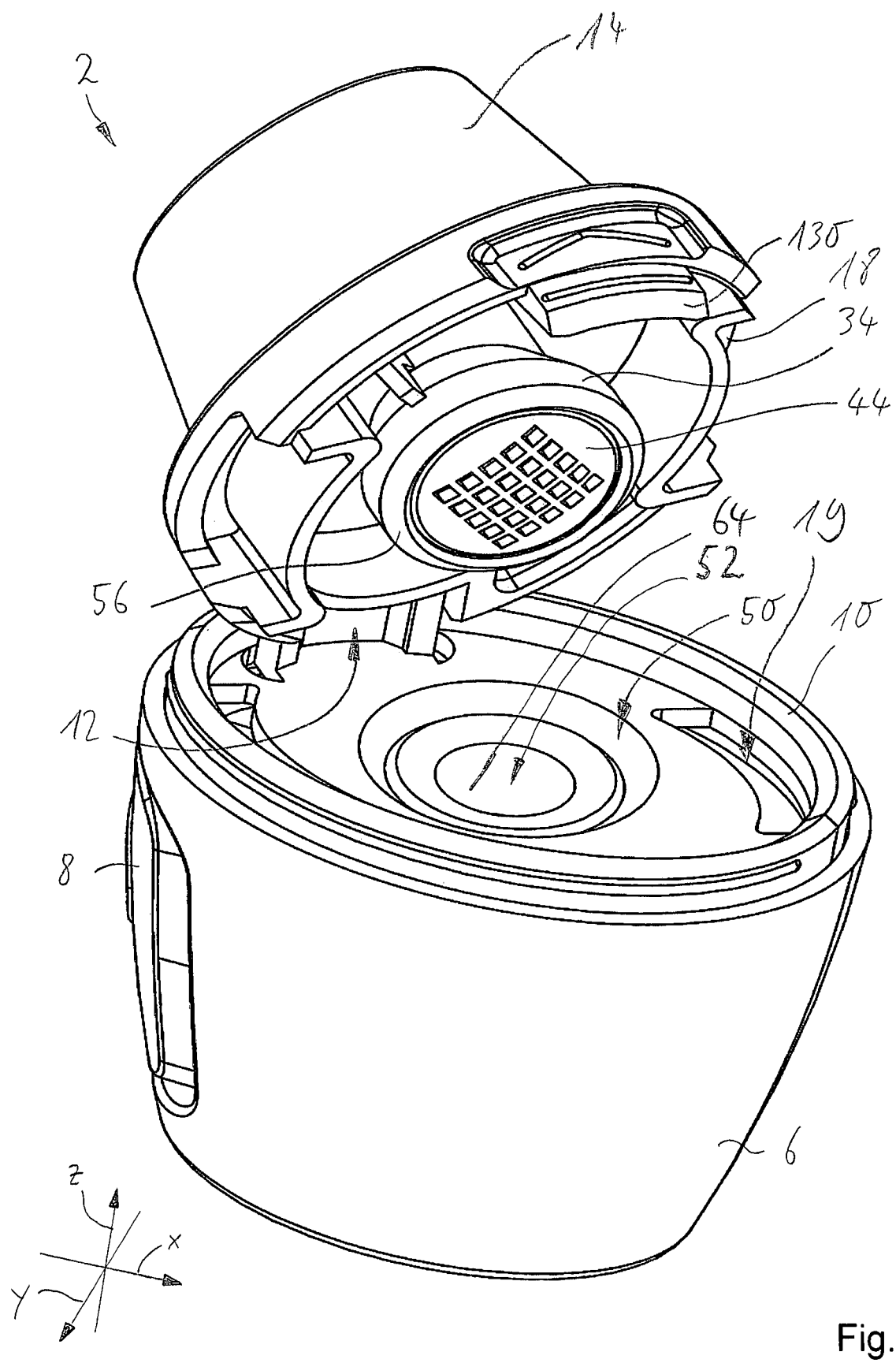
FIGS. 6, 8, and 9 each depicts a schematic perspective view of the dry powder inhaler.

FIG. 6 shows a schematic perspective view of the dry powder inhaler 2 with an opened mouth piece. A latch 130 of the mouth piece 14 engages the base body 10. The mesh piece 44 provides chessboard-like openings. The hinge 12 is arranged towards the actuation button 8. The base body 10 comprises an opening 19 which corresponds to the opening 18. The opening 19 of the base body leads into a volume between the base body 10 and the covering body 6 in order to provide an air passage from the outside of the inhaler into the capsule chamber 64.

Figure 7:
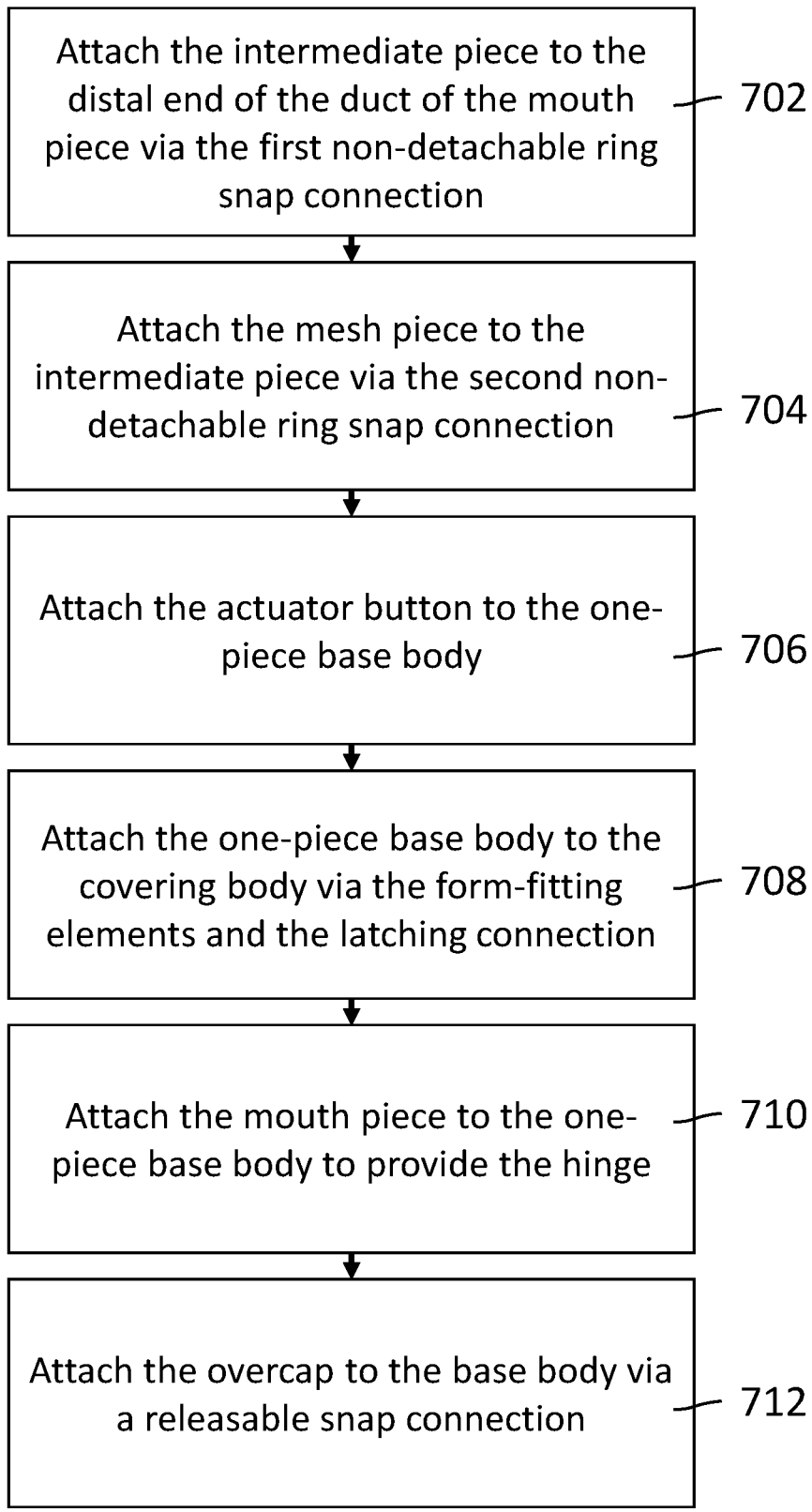
FIG. 7 shows a schematic flow diagram.

FIG. 7 shows a schematic flow diagram to manufacture the inhaler. In a step 702 the intermediate piece is attached to the distal end of the duct of the mouth piece via the first non-detachable ring snap connection. In a step 704 the mesh piece is attached to the intermediate piece via the second non-detachable ring snap connection. In a step 706 the actuator button is attached to the one-piece base body, which involves the insertion of the needles into corresponding guiding sections, the insertion of the spring, and the insertion of the guiding members in the respective guiding channels. In a step 708 the one-piece base body is attached to the covering body via the form-fitting elements and the latching connection. In a step 710 the mouth piece is attached to the one-piece base body to provide the hinge. In a step 712 the overcap is attached to the base body via a releasable snap connection.

Figure 8:
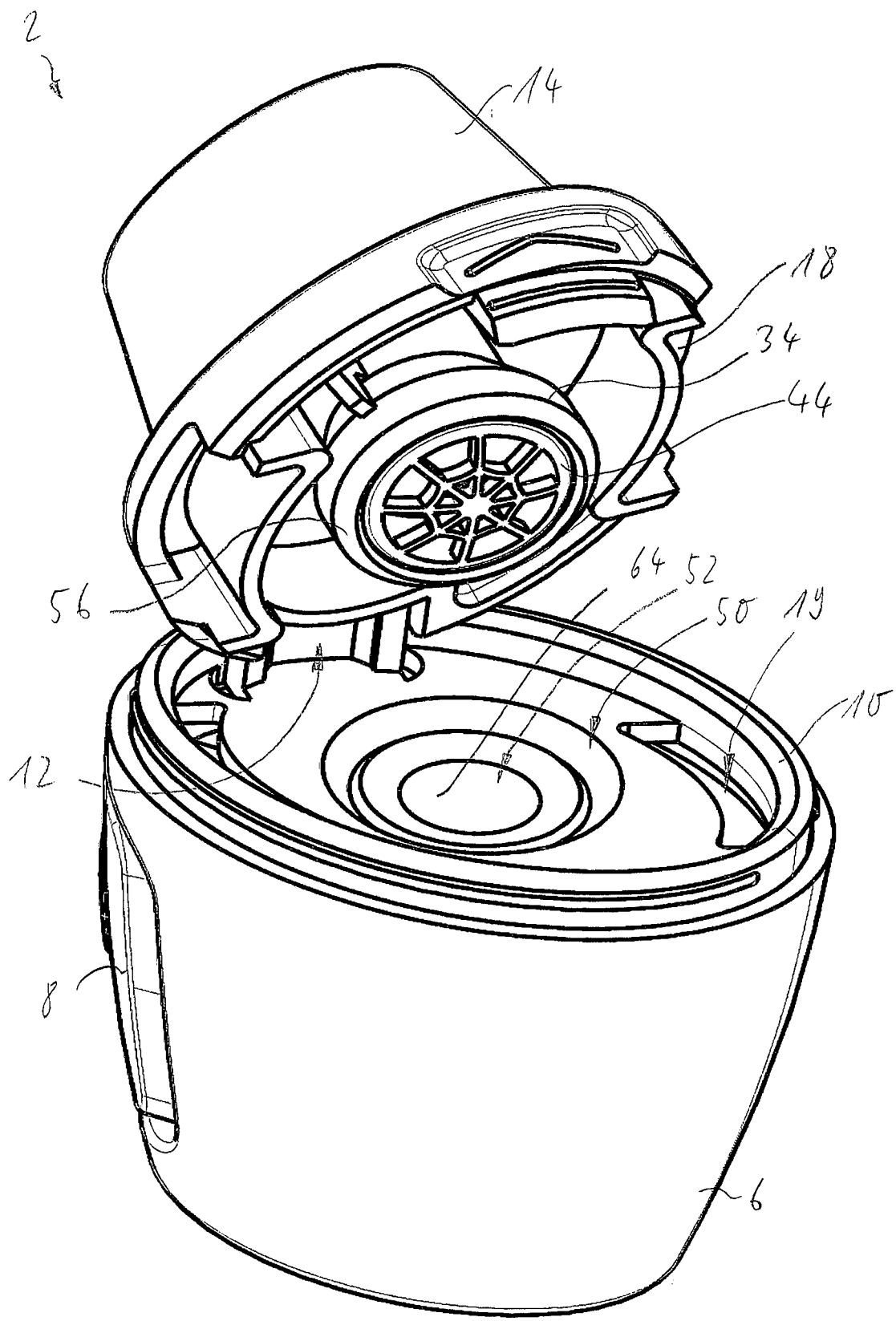

FIG. 8 shows a schematic perspective view of an embodiment of the dry powder inhaler 2. With difference to FIG. 6 the mesh piece 44 provides a cobweb-like opening structure.

Figure 9:
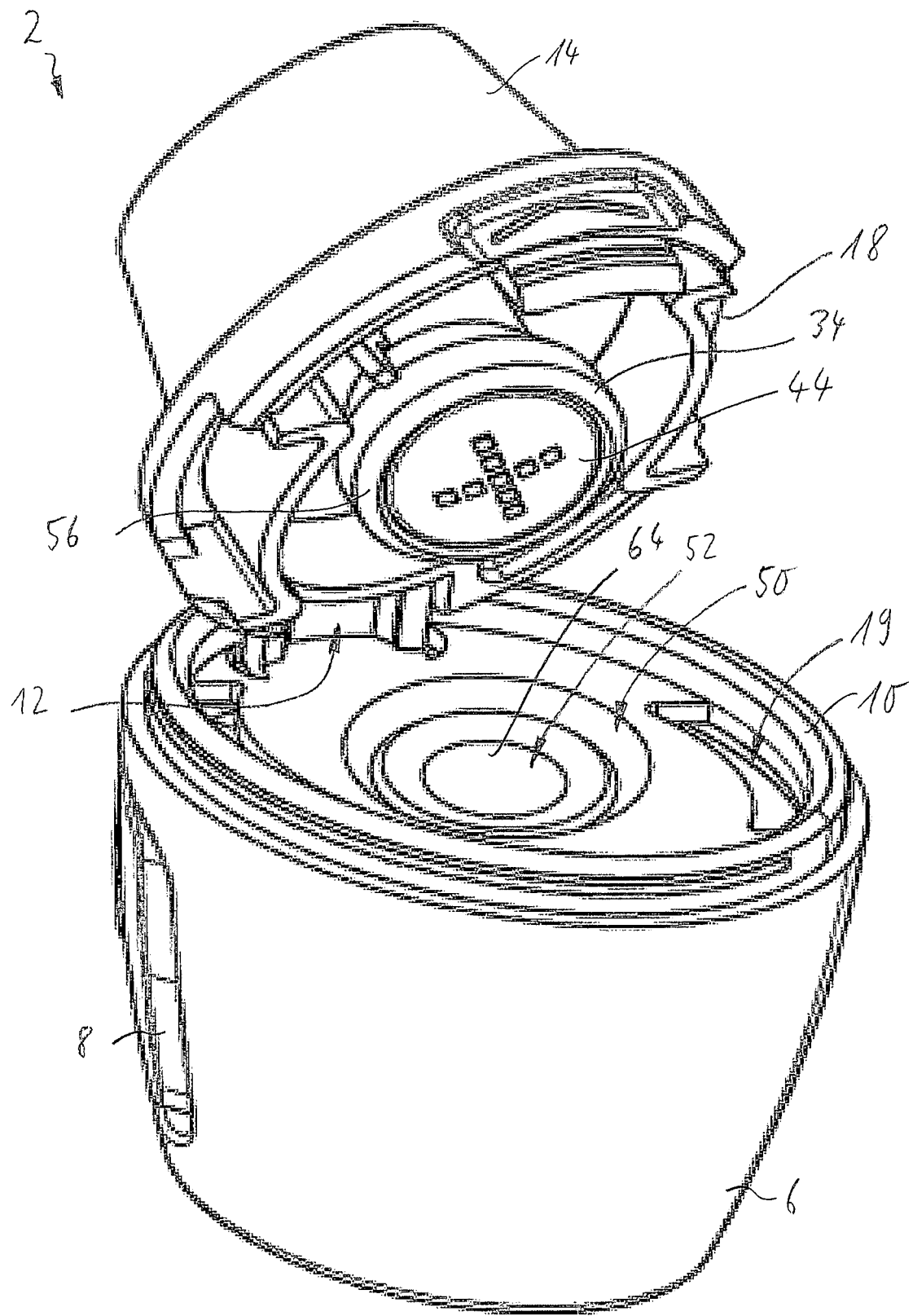

FIG. 9 shows a schematic perspective view of an embodiment of the dry powder inhaler 2. With difference to FIG. 6 the mesh piece 44 provides a cross-like opening structure.

The invention claimed is:

1. A dry powder inhaler for a capsule containing dry powder, the dry powder inhaler comprising:
 a mouth piece with a mouth portion, wherein an opening of the mouth portion leads into a duct;
 an intermediate piece, which is attached to a distal end of the duct of the mouth piece;
 a mesh piece, which is attached to the intermediate piece;
 a covering body;
 a one-piece base body comprising a capsule chamber portion and being attached to the covering body, wherein a base body opening, which is arranged towards the mouth piece, leads into a capsule chamber of the capsule chamber portion, wherein the duct and the capsule chamber extend along a common longitudinal axis when the mouth piece abuts the base body, and wherein a hinge directly connects the mouth piece and the one-piece base body, wherein the one-piece base body comprises an annular-shaped groove arranged around the base body opening, and wherein the intermediate piece comprises an annular-shaped distal end for engaging with the annular-shaped groove; and
 an actuator button movable relative to the one-piece base body from a normal position to a perforation position along an actuation direction, wherein the actuation direction is perpendicular to the longitudinal axis, and wherein perforation needles attached to the actuator button extend into the capsule chamber when the actuator button is in the perforation position.

2. The dry powder inhaler of claim 1, wherein the intermediate piece is held only by a first ring snap connection, wherein the mesh piece is held only by a second ring snap connection.

3. The dry powder inhaler of claim 1, wherein an inner diameter of the intermediate piece and/or the mesh piece is greater than an inner diameter of the duct.

4. The dry powder inhaler of claim 1, wherein an inner diameter of the duct of the mouth piece is smaller than an inner diameter of the capsule chamber.

5. The dry powder inhaler of claim 1, wherein the one-piece base body is attached to the covering body by a latching connection.

6. The dry powder inhaler of claim 5, wherein the one-piece base body comprises a ratchet of the latching connection, and an outer surface opposed to the ratchet; and
 wherein the covering body comprises:
  a first inner protrusion for a third latching connection, the first inner protrusion comprising a hole receiving the ratchet of the one-piece base body; and
  a second inner protrusion abutting said outer surface of the one-piece base body.

7. The dry powder inhaler of claim 5, wherein the covering body further comprises an opening with an inward cut-out for receiving a plate portion of the one-piece base body, and wherein the one-piece base body further comprises the plate portion with an outward edge contacting at least partly the inward cut-out.

8. The dry powder inhaler of claim 1, wherein the actuator button comprises guiding members, which protrude from a button body, and embrace at least partly the capsule chamber portion.

9. The dry powder inhaler of claim 8, wherein a guiding channel is formed for each of the guiding members by an inner support protrusion of the covering body and the capsule chamber portion.

10. A method of manufacturing the dry powder inhaler according to claim 1, the method comprising:
 attaching the intermediate piece to the distal end of the duct of the mouth piece;
 attaching the mesh piece to the intermediate piece;
 attaching the actuator button to the one-piece base body;
 attaching the one-piece base body to the covering body; and
 attaching the mouth piece to the one-piece base body to provide the hinge, wherein the one-piece base body comprises an annular-shaped groove arranged around the base body opening, and wherein the intermediate piece comprises an annular-shaped distal end for engaging with the annular-shaped groove.

11. A dry powder inhaler for a capsule containing dry powder, the dry powder inhaler comprising:
 a mouth piece with a hinge section;
 a covering body; and
 a one-piece base body comprising a capsule chamber portion and being attached to the covering body, wherein a hinge directly connects the mouth piece and the one-piece base body, wherein the hinge section of the mouth piece is connected to a hinge section of the one-piece base body via a ball joint snap-on connection for pivoting around a hinge axis, wherein the one-piece base body is attached to the covering body by a latching connection, wherein the one-piece base body comprises a ratchet of the latching connection, and an outer surface opposed to the ratchet; and wherein the covering body comprises:
  a first inner protrusion for a third latching connection, the first inner protrusion comprising a hole receiving the ratchet of the one-piece base body; and
  a second inner protrusion abutting said outer surface of the one-piece base body.

12. The dry powder inhaler of claim 11, wherein the hinge axis of the hinge is arranged in an inclined angle within the range of 40° to 50° with respect to an actuation direction.

13. The dry powder inhaler of claim 11, wherein the hinge axis is arranged in a plane perpendicular to a central longitudinal axis of the inhaler.

14. A dry powder inhaler for a capsule containing dry powder, the dry powder inhaler comprising:
 a mouth piece with a hinge section;
 a covering body; and
 a one-piece base body comprising a capsule chamber portion and being attached to the covering body, wherein a hinge directly connects the mouth piece and the one-piece base body, wherein the hinge section of the mouth piece is connected to a hinge section of the one-piece base body via a ball joint snap-on connection for pivoting around a hinge axis, wherein the one-piece base body is attached to the covering body by a latching connection, wherein the covering body further comprises an opening with an inward cut-out for receiving a plate portion of the one-piece base body, and wherein the one-piece base body further comprises the plate portion with an outward edge contacting at least partly the inward cut-out.

* * * * *

UNITED STATES PATENT AND TRADEMARK OFFICE
CERTIFICATE OF CORRECTION

| | |
|---|---|
| PATENT NO. | : 11,951,247 B2 |
| APPLICATION NO. | : 16/772083 |
| DATED | : April 9, 2024 |
| INVENTOR(S) | : Victor Esteve |

It is certified that error appears in the above-identified patent and that said Letters Patent is hereby corrected as shown below:

On the Title Page

Item (73) The Assignee. The second word "*Lmportatodra*" should be corrected to read "*Importadora*".

Signed and Sealed this
Ninth Day of July, 2024

Katherine Kelly Vidal
*Director of the United States Patent and Trademark Office*